United States Patent [19]
Sanders et al.

[11] Patent Number: 5,540,689
[45] Date of Patent: Jul. 30, 1996

[54] APPARATUS FOR SECURING A ROD ADJACENT TO A BONE

[76] Inventors: Albert E. Sanders, 7107 Brookside La.; James O. Sanders, 530 Grandview Pl., both of San Antonio, Tex. 78209; Robert B. More, 1811 Running Brook, Austin, Tex. 78723

[21] Appl. No.: 215,182

[22] Filed: Mar. 21, 1994

Related U.S. Application Data

[60] Continuation-in-part of Ser. No. 189,192, Jan. 31, 1994, which is a division of Ser. No. 956,673, Oct. 5, 1992, Pat. No. 5,290,289, which is a continuation-in-part of Ser. No. 526,601, May 22, 1990, abandoned.

[51] Int. Cl.⁶ .......................... A61B 17/70; A61B 17/84
[52] U.S. Cl. .......................... 606/61; 606/78; 606/151; 403/28; 24/531; 24/570
[58] Field of Search ............................ 606/61, 78, 151; 623/17; 403/28, 110, DIG. 9; 24/DIG. 22, 531, 570

[56] References Cited

U.S. PATENT DOCUMENTS

| | | | |
|---|---|---|---|
| 4,120,130 | 10/1978 | Puschkarski | 403/110 X |
| 4,170,990 | 10/1979 | Baumgart et al. | 606/78 |
| 4,596,483 | 6/1986 | Gabriel | 403/28 |
| 5,358,511 | 10/1994 | Gatturna et al. | 606/232 |
| 5,391,168 | 2/1995 | Sanders et al. | 606/61 |

FOREIGN PATENT DOCUMENTS

| | | | |
|---|---|---|---|
| 1136803 | 1/1985 | U.S.S.R. | 606/61 |
| 1152582 | 4/1985 | U.S.S.R. | 606/78 |
| 1537236 | 1/1990 | U.S.S.R. | 606/78 |

*Primary Examiner*—David H. Willse
*Attorney, Agent, or Firm*—Donald R. Comuzzi; Christopher L. Makay

[57] ABSTRACT

A method and implant for the surgical treatment of scoliosis is disclosed. The method involves the segmental fixation of a rigid rod or rods to the abnormally curved portion of the spine. The rod is constructed of a shape-memory alloy such as nitinol. Prior to implementation, the rod is annealed and contoured into an ideal shape for a given patient. At the time of surgery, the rod is deformed to accommodate the existing curvature of the patient's spine and segmentally fixed thereto using novel bone clamps. The rod is then inductively heated to the transition temperature post-operatively to effect shape recovery and thereby apply corrective forces to the spine.

8 Claims, 2 Drawing Sheets

APPARATUS FOR SECURING A ROD ADJACENT TO A BONE

BACKGROUND OF THE INVENTION

This application is a continuation-in-part application of application Ser. No. 08/189,192, filed Jan. 31, 1994, which is a divisional application of application Ser. No. 07/956,673, filed Oct. 5, 1992, now U.S. Pat. No. 5,290,289, which is a continuation-in-part application of application Ser. No. 07/526,601, filed May 22, 1990, now abandoned.

The present invention relates to an improvement over prior methods and apparatus for surgically treating abnormal curvatures of the spine.

The normal spine possesses some degree of curvature in three different regions. The lumbar spine is normally lordotic (i.e., concave posteriorly), the thoracic spine kyphotic (i.e., convex posteriorly), and the cervical spine also lordotic. These curvatures are necessary for normal physiologic function, and correction is desirable when the spine has either too much or too little curvature in these regions as compared with the norm. A more common abnormality, however, is lateral deviation of the spine or scoliosis.

The first successful internal fixation method for surgically treating scoliosis involves the use of the Harrington instrumentation system. In this method, a rigid rod having hooks at each end is implanted adjacent the concave side of the scoliotic spine. The hooks engage in the facet joints of a vertebra above and under the laminae of a vertebra below the abnormally curved region. At the time of surgery, the spine is manually straightened to a desired extent. The distraction rod is then used to maintain the correction by exerting vertical forces at each end on the two aforementioned vertebra. The rod commonly has a ratcheted end over which the hooks are slidably mounted and locked in place. The effective length of the rod may thus be adjusted to an appropriate length for exerting the distractive force.

The Harrington distraction rod, because its corrective force is purely distractive, tends to correct curvature in both the frontal and sagittal planes. This means that unwanted loss of normal thoracic kyphosis or lumbar lordosis may inadvertently be produced. To compensate for this, a compression rod is sometimes placed on the convex side of the scoliotic spine. Another variation on the Harrington method which addresses the same problem is to contour the distraction rod in the sagittal plane in accordance with the kyphotic and lordotic curvatures of the normal spine. This may, however, reduce the ability to apply large corrective forces in the frontal plane due to column buckling.

The Harrington instrumentation system has been used successfully but exhibits some major problems. It requires a long post-operative period of external immobilization using a cast or brace. Also, because the distraction rod is fixed to the spine in only two places, failure at either of these two points means that the entire system fails. Failure at the bone-hook interface is usually secondary to mechanical failure of the bone due to excess distractive force.

Another method was thus developed utilizing the concept of segmented fixation. In this method, the spine is manually corrected to a desired degree as before. A rod is then fixed to the spine at multiple points by means of the sublaminar wires (i.e., wires running underneath the lamina of the vertebra and around the rod). The multiple fixation sites add to the stability of the system and make post-operative external immobilization frequently unnecessary. Segmental fixation also makes failure of the entire system much less probable. The possibility that loss of correction will occur post-operatively is also made less likely.

Segmental fixation may be used with a Harrington distraction rod or, as is more usually the case, with a pair of so-called Luque or L-rods. L-rods have a long segment which is aligned with the spine and a short segment perpendicular to the long segment. The short segments of the L-rods are inserted in notches or holes made in the spinous processes of vertebra above and below the deformed region of the spine. By placing the two L-rods on opposite sides of the spine and in opposite longitudinal orientation, the entire system is made less vulnerable to vertical migration.

Whether one rod or two is used in the segmental fixation method, the corrective forces are applied in a transverse direction via the sublaminar or spinous process wires rather than in a longitudinal direction as with a Harrington distraction rod. Since the corrective forces are applied transversely, the integrity of the system is not compromised when the rods are contoured to accommodate normal anatomic kyphosis and lordosis.

Another problem with both of the methods described above is their lack of effectiveness in producing rotatory correction in the transverse plane. The longitudinal forces of the Harrington distraction method, with or without an additional compression rod, do not contribute a corrective torque necessary for transverse plan derotation. The segmental fixation method could theoretically apply corrective forces in the transverse plane through the connecting sublaminar wires, but this is dependent on the sequence of wire tightening during implantation and is, as a practical matter, very difficult to achieve. This is unfortunate because scoliosis is generally a three-dimensional deformity requiring some correction in the transverse plane.

The shape-memory alloy, nitinol, has also been attempted as a Harrington rod without segmental fixation to correct scoliosis. This was unsuccessful because the corrective forces could not be transmitted effectively from the rod to the spine.

It is an object of the present invention to provide a method and instrumentation for the surgical treatment of scoliosis using segmental fixation which provides rotatory correction in the transverse plane.

It is a further object of the present invention to provide a method and instrumentation for applying corrective forces to the scoliotic spine while minimizing the forces which must be withstood by the fixation points, thereby lessening the possibility of metal bone interface failure.

It is a still further object of the present method to apply corrective forces to the scoliotic spine in a manner which minimizes the possibility of damage to the spinal cord.

It iS a still further object of the present method to allow the easy technical insertion of an implant for correcting scoliosis by deforming the implant to match the shape of the patient's spine.

SUMMARY OF THE INVENTION

The present invention is a method and apparatus which uses a shape memory alloy, such as nitinol, to enhance the function of segmental spine instrumentation in the treatment of scoliotic spinal deformities. Essential to the present invention is that a correction rod which may be either circular or non-circular must be segmentally attached to the spine so as to impart transverse and torsional corrective forces to the spine. Furthermore, even though the rod must be affixed to the spine, during some stages of correction it must be free to slide along the spine, while during others it must be rigidly coupled to the spine. Segmental affixation of the rod combined with rod mobility and alternate rod rigidity is accomplished utilizing bone holding devices, such as hooks, screws, or the like, fashioned from shape memory materials such as nitinol.

Each bone holding device comprises a rod housing formed integrally with a bone hook which is originally sized to securely fit the vertebrae. To mount the bone clamp to an individual vertebra of the spine during surgery, each bone hook of the bone clamp is cooled and expanded to a size larger than the individual vertebra. The bone hook is then placed about the vertebra and heated until its distal end encircles a portion of the vertebra to firmly secure the entire bone clamp to the vertebra. The above process is then repeated until the number of bone clamps necessary to affix the rod to the spine have been connected to the vertebrae.

To permit the rod to slide along the spine during some stages of correction, yet be held completely rigid during others, each of the rod housings include a pincer. The distance between each claw of the pincer originally is greater than the diameter of a circular rod or the longest side of a non-circular rod. That shape of the rod housings improves over prior bone clamps because it allows the rod to be placed directly and simultaneously into each of the rod housings.

Thus, to mount the rod into the rod housings, it is placed within the pincer of each rod housing, whereupon each pincer is crimped such that their claws encircle the rod. Although the initial clamping of the pincers results in the encircling of the rod by the claws to provide a bearing-like fit and surface for the rod within each rod housing, the friction between the rod housings and the rod is insufficient to prevent the rod from sliding freely within the rod housings. That is, the inner surface of each the rod housings contact the correction rod; however, the frictional forces developed between the two surfaces are not sufficient to prevent rod movement. When it is necessary to prevent rod movement, heat is applied to pincers of the rod housings, causing their claws to further encircle the rod such that the frictional forces therebetween are sufficient to prevent the rod from sliding within the rod housings.

An alternative bone clamp comprises a bone hook having a pincer-type shape formed integrally with a rod housing. To mount the bone clamp to an individual vertebra of the spine during surgery, the bone clamp, which originally is sized to securely fit the vertebrae, is cooled and expanded to a size larger than the vertebra. The bone hook is then placed about the vertebra and heated until its pincers snugly encircle the vertebra, thereby, firmly attaching the entire bone clamp to the vertebra. The above process is then repeated until the number of bone clamps necessary to affix the rod to the spine are connected to the vertebrae.

Another alternative bone clamp comprises two separate members which are coupled together during surgery to form the bone clamp. Each member is identical and comprises a claw formed integrally with a rod housing wherein the inner face of the rod housing edge integrally formed with the claw is provided with a hole on one side and a connector rod having a hook at its end on the other. To mount the bone clamp on a vertebra of the spine during surgery, the two members are first cooled in order to straighten the hook on the end of each member and expand the claws. The two members are then placed in opposed relation about the vertebra. That is, the claws face each other and surround the vertebra while the connector rod of each member fits through the hole provided in the opposite member. Next, the members are heated which causes the hook at the end of the connector rods to reform, thereby, securing the two members together and preventing their uncoupling. In addition, the claws encircle the vertebra to firmly connect the bone clamp. The above process is then repeated until the number of bone clamps necessary to affix the rod to the spine have been connected to the vertebrae.

To permit the rod to slide along the spine during some stages of correction, yet be held completely rigid during others, each of the rod housings of the alternative bone clamps may be fitted with a blocker. The blocker comprises a tube constructed of a shape memory material such as nitinol which is circularly-shaped so that the edges of the tube overlap. The original shape of the blockers is such that their outer diameters are the same as the correction rod. Additionally, the overlapping shape of the blockers is chosen because it permits their inner diameters to be significantly increased or decreased with only a small concurrent change in their outer diameters. To mount each individual blocker within a rod housing, each blocker is cooled to allow its inner diameter to be expanded and its outer diameter to shrink slightly which permits the blocker to form a cylinder sliding on the rod housing while the correction rod easily fits within each blocker. However, although the inner diameters of the blockers are large enough to permit the rod to slide freely, those inner diameters are still small enough to provide a bearing-like fit and surface for the correction rod to the rod housings. That is, the inner surfaces of the blockers contact the correction rod; however, the frictional forces developed between the two surfaces are not sufficient to prevent correction rod movement. When it is necessary to prevent correction rod movement, heat is applied to the blockers, causing them to return to their original shape, thereby completely clamping the correction rod firmly within the rod housing. After the blockers have returned to their original shape, the frictional forces between the inner surfaces of the blockers and the correction rod are sufficient to prevent the rod from sliding.

To practice the present invention, the correction rod is first heated to a temperature at which the crystalline structure of nitinol is entirely in the parent phase. A transformation temperature which is in a 10° C. range of normal body temperature is selected for rod construction. The rod is then contoured to the ideal shape to which it is desired to correct the patient's spine. After that is accomplished, the rod is cooled to the point where the martensite crystal structure replaces the austenitic phase structure. The rod may now be further deformed but will "remember" the original ideal shape upon being heated to the shape transition temperature.

At the time of surgery, the rod is deformed to a shape which accommodates the existing shape of the patient's scoliotic spine. During this deformation, the temperature of the rod must be maintained below the shape transition temperature. The rod is then segmentally fixed to spine as described above. Some amount of correction may be attained at surgery, but it should be less than the ideal shape to which the rod memory is set so that a potential for shape recovery work exists in the implanted rod. Thus, post-operatively, additional correction may be attained by heating the rod to the shape transition temperature. Because of the segmental fixation, and the fact that the shape recovery of the alloy is a local phenomena, shape recovery forces may be confined to certain vertebral levels as desired by only applying the heat to certain local areas of the rod. Furthermore, the extent of heating, and, thus, the amount of shape recovery force, may be controlled so that the rod moves to its ideal shape to the degree that the spine can withstand without risking neural damage or failure of the metal-bone interface. Also, rotation of the spine due to scoliosis may be corrected by the torque exerted by the rod.

DETAILED DESCRIPTION OF THE INVENTION

Figure 1:
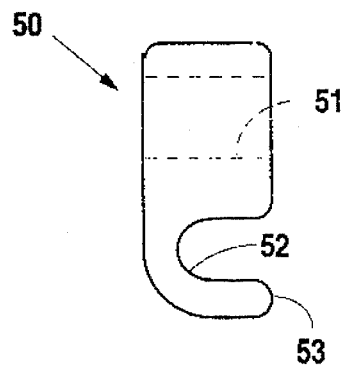
FIG. 1 is a side elevation view depicting the bone clamp of the present invention.

In accordance with the present invention, the implantable rod used to apply corrective forces to the spine is constructed of a shape-memory alloy such as nitinol. Nitinol is a nearly equal atomic ratio of nickel and titanium which exhibits a shape-memory effect. That is, after being deformed (up to about 8% strain) the material remembers its original annealed shape and will return to that original shape when heated above the shape transition temperature. In so doing, the alloy converts heat energy into mechanical work. The mechanical work done while the material is undergoing shape recovery can be much greater than that originally imparted during the initial plastic deformation.

In order for an alloy to exhibit the shape-memory effect, it must be a crystalline structure which can shift into the so-called parent phase when it is subjected to a certain temperature condition and then shift into the configuration known as martensite when the temperature is lowered. The alloy is first annealed to a specified shape. The alloy may then be heated to a temperature high enough that the crystalline structure assumes the parent phase or which is referred to in the art as the austenite configuration. Next, the alloy is cooled until it reverts to the martensite configuration. The alloy may now be further deformed randomly but will return to the original shape when heated to a temperature above that at which the martensite returns to the parent phase. The specific transitional temperature at which the phase transition occurs can be controlled by controlling the exact nickel to titanium ratio.

The use of shape-memory alloys for use in the surgical correction of scoliosis has been investigated before, using a Harrington distraction rod constructed of nitinol, but the corrective forces could not be applied effectively to the spine. Several unique advantages occur, however, when the properties of a shape-memory alloy are utilized by a segmental fixation method for correcting scoliosis. These include rotatory correction in the transverse plane, less applied force at the bone-metal interface which increase the efficiency of transverse forces in correcting severely deformed spines in the frontal plane, localized correction applied post-operatively while the patient is monitored to minimize the risk of neural damage, the fact that the rod can be contoured to the pre-operative shape of the patient's spine. The corrective forces can be effectively applied to the spine.

A single rod or a plurality of rods constructed of nitinol is first deformed while in the parent phase crystalline configuration to the ideal shape to which it is desired to eventually correct a particular patient's spine. The rod is then cooled until the martensite transformation occurs. While maintaining the rod below the shape transition temperature, the rod may be deformed to conform to present shape of the patient's spine, which may include twisting. Alternatively, the rod may deviate somewhat from the spine's pre-operative shape in order to apply some correction during surgery. Because all of the corrective potential of the rod is stored as shape-memory, the rod can be positioned to lie immediately adjacent to the spine all along its length. This improves the rigidity of whatever technique of segmental fixation is used because the rod may rest firmly against the spine. In prior methods of segmental fixation, this cannot be accomplished because the rod must necessarily be shaped differently than the patient's pre-operative spine. Attempts to approximate such a rod to a lamina by, for example, twisting the wires, risks wire breakage and damage to the patient's spine.

The rod or rods which may be either circular or non-circular is segmentally fixed to the spine using the apparatus and method described herein in order to provide sufficient fixation rigidity and strength. Because, as explained below, the corrective forces are applied gradually in a manner which lessens the stresses borne by the individual fixation points, the present method employs bone clamps (described herein) rather than sublaminar wires to segmentally fix the rod to the spine. The present invention, therefore, by avoiding invasion of the neural canal, greatly reduces the risk of damage to the spinal cord. However, it is to be understood that techniques employing existing devices such as wires, hooks, tape, or screws could be used to secure the correction rod to the scoliotic spine.

Referring to FIGS. 1–5, the preferred embodiment of the bone holding device will be described. Bone holding device 50 is constructed of nitinol and comprises rod housing 51 which includes pincer 54 and is formed integrally with bone hook 52 which is originally sized to securely fit about the vertebrae and oriented transverse to pincer 54 to facilitate the mounting of rod housing 51 adjacent to a vertebra. To mount bone holding device 50 to an individual vertebra of the spine during surgery, bone hook 52 is cooled and expanded to a size larger than the individual vertebra. Claw 53 of bone hook 52 is then placed about the vertebra and heated until its distal end encircles a portion of the vertebra to firmly secure bone holding device 50 to the vertebra. The above process is then repeated until the number of bone holding devices necessary to affix the rod to the spine have been connected to the vertebrae.

Figure 2:
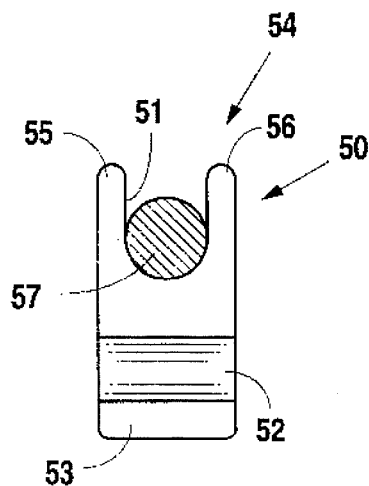
FIG. 2 is a front elevation view depicting the bone clamp of the present invention fitted with a circular rod in its untransformed state.
Figure 3:
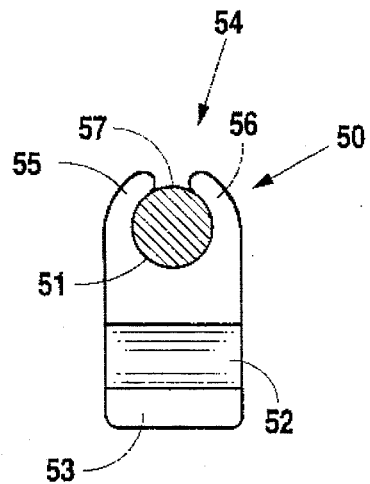
FIG. 3 is a front elevation view depicting the bone clamp of the present invention fitted with a circular rod in its transformed state.

To permit the rod to slide along the spine during some stages of correction, yet be held completely rigid during others, each of rod housings 51 include pincer 54. The distance between claws 55 and 56 of pincer 54 originally is greater than the diameter of a circular rod or the longest side of a non-circular rod. That shape of rod housings 51 improves over prior bone holding devices because it allows rod 57 to be placed directly and simultaneously into each of rod housings 51 of bone holding device 50. However, the specific shape of the inner surface of rod housing 51 depends upon whether a circular or a non-circular rod is to be used. That is, if a circular rod is to be used, the inner surface of rod housing 51 includes a curve which receives rod 57 as depicted in FIGS. 2 and 3. Alternatively, if a non-circular rod is to be used, the inner surface of rod housing 51 includes three straight edges which receive rod 57 as depicted in FIGS. 4 and 5.

Figure 4:
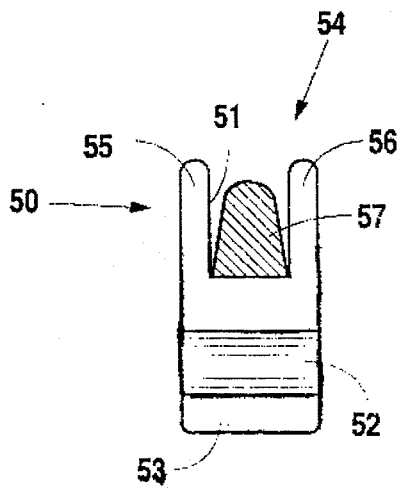
FIG. 4 is a front elevation view depicting the bone clamp of the present invention fitted with a non-circular rod in its untransformed state.
Figure 5:
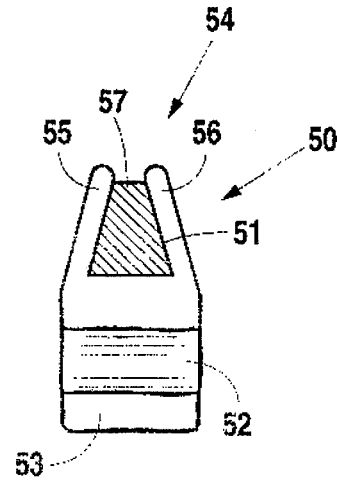
FIG. 5 is a front elevation view depicting the bone clamp of the present invention fitted with a non-circular rod in its transformed state.

Thus, to mount rod 57 in a plurality of bone holding devices 50 connected to the vertebra of the spine as described above, it is passed through the opening of each pincer 54 and placed within each rod housing 51 (See FIGS. 2 or 4). After rod 57 has been placed within rod housings 51, each pincer 54 is crimped so that claws 55 and 56 encircle rod 57 (See FIGS. 3 or 5). Although the initial clamping of pincer 54 results in the encircling of rod 57 by claws 55 and 56 to provide a bearing-like fit and surface for rod 57 within each rod housing 51, the friction between rod 57 and rod housings 51 is insufficient to prevent rod 57 from sliding freely within rod housings 51. That is, the inner surface of each rod housings 51 contact rod 57; however, the frictional forces developed between the two surfaces are not sufficient to prevent rod 57 from moving. When it is necessary to secure rod 57 within rod housings 51, heat is applied to pincers 54, causing claws 55 and 56 to further encircle rod 57 such that the frictional forces therebetween are sufficient to prevent rod 57 from sliding within rod housing 51.

Figure 6:
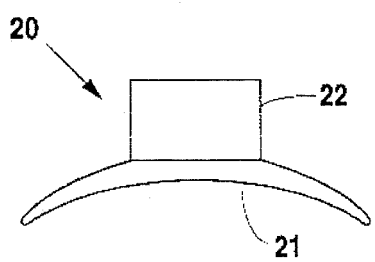
FIG. 6 is a side elevation view depicting the cooled state of an alternative embodiment of the bone clamp.
Figure 7:
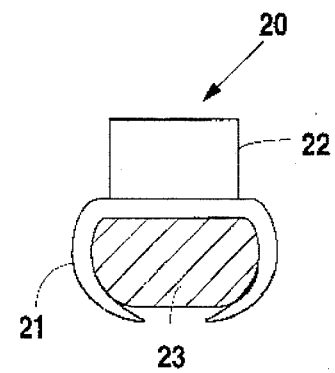
FIG. 7 is a side elevation view depicting the heated state of the alternative embodiment of the bone clamp.

Referring to FIGS. 6–7, the first alternative embodiment of the bone clamp according to the present invention will be described. Bone clamp 20 is constructed of nitinol and comprises bone hook 21 having a pincer-type shape formed integrally with rod housing 22. During surgery in order to mount bone clamp 20 to an individual vertebra of the spine, bone clamp 20, which originally is sized to securely fit the vertebrae, is cooled and expanded to a size larger than the vertebra (See FIG. 6). Bone hook 21 is then placed about vertebra 23 and heated until its pincers snugly encircle vertebra 23, thereby, firmly attaching bone clamp 20 to vertebra 23, (See FIG. 7). The above process is then repeated until the number of bone clamps necessary to affix the rod to the spine have been connected to the vertebrae.

Figure 8:
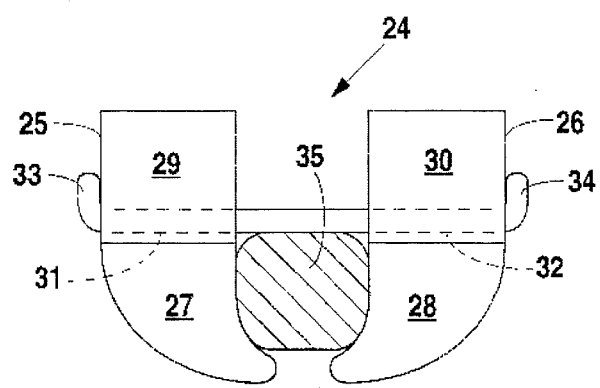
FIG. 8 is a side elevation view depicting a second alternative embodiment of the bone clamp.
Figure 9:
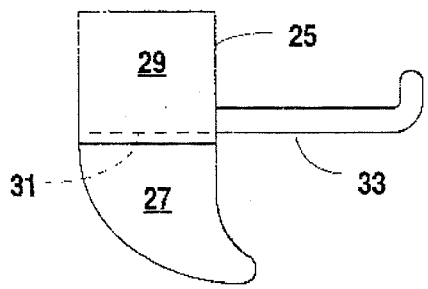
FIG. 9 is a side elevation view depicting the heated state of one member of the bone clamp of the second alternative embodiment.
Figure 10:
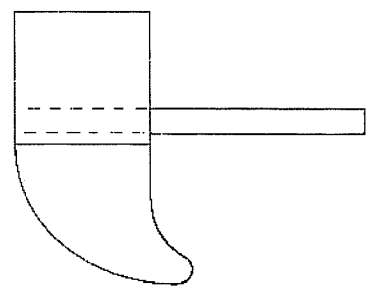
FIG. 10 is a side elevation view depicting the cooled state of one member of the bone clamp of the second alternative embodiment.

Referring to FIGS. 8–10, the second alternative embodiment of the bone clamp according to the present invention will be described. Bone clamp 24 is constructed of nitinol and comprises first and second members 25 and 26 which are coupled together during surgery to form bone clamp 24 (See FIG. 8). Members 25 and 26 are identical and comprise claws 27,28 formed integrally with rod housings 29,30 wherein the inner face of the rod housing edge integrally formed with claws 27,28 are provided with holes 31,32 on one side and connector rods 33,34 having a hook at its opposite end (See FIG. 9). To mount bone clamp 24 onto vertebra 35 of a spine, first and second members 25 and 26 are cooled in order to straighten the hooks on the end of each member 25,26 and expand claws 27,28 (See. FIG. 10). Members 25,26 are then placed in opposed relation about vertebra 35. That is, claws 27,28 face each other and surround vertebra 35 while connector rods 33,34 of each member 25,25 fit through holes 31,32 provided in the opposite member. Next, members 25,26 are heated which causes the hook at the end of connector rods 33,34 to reform, thereby, securing members 25,26 together and preventing their uncoupling. In addition, claws 27,28 encircle vertebra 35 to firmly connect bone clamp 24. The above process is then repeated until the number of bone clamps necessary to affix the rod to the spine have been connected to the vertebrae.

Although segmental affixation is essential to the present invention so that the correction rod can impart transverse and torsional corrective forces to the spine, it is also essential that the correction rod slide freely along the spine during some stages of correction, while during others it must be rigidly coupled to the spine. To permit the correction rod to slide freely along the spine during some stages of correction, yet be held completely rigid during others, rod housing 22 of bone clamp 20 and rod housings 29,30 of bone clamp 24 may be fitted with a blocker.

Figure 11:
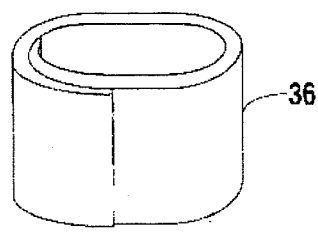
FIG. 11 is a perspective view depicting the blocker utilized in both alternative embodiments of the bone clamps.
Figure 12:
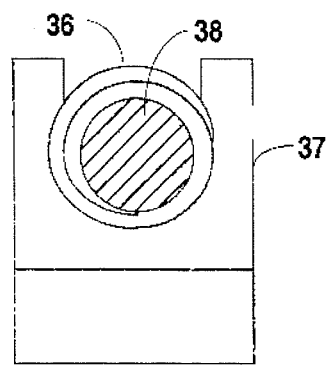
FIG. 12 is a end elevation view depicting the mounting of the correction rod within the rod housing of one of the alternative bone clamps.

Referring to FIGS. 11 and 12, the blockers, rod housings, and affixation of the correction rod within the housing will be described. Although the affixation of the correction rod to the spine is described with reference to a single rod housing and blocker, it is to be understood that all the blockers and rod housings operate similarly. Blocker 36 is constructed of nitinol and comprises a tube which is circularly-shaped such that its edges overlap (See FIG. 11). The original shape of blocker 36 is such that its outer diameter is the same as the inner diameter of rod housing 37, and its inner diameter is the same as correction rod 38. Additionally, the overlapping shape of blocker 36 is chosen because it permits its inner diameter to be significantly increased or decreased with only a small concurrent change in its outer diameter. To mount blocker 36 within rod housing 37, blocker 36 is cooled to allow its inner diameter to be expanded and its outer diameter to shrink slightly which permits blocker 36 to securely fit within rod housing 37 while correction rod 38 easily fits within blocker 36. However, although the inner diameter of blocker 36 is large enough to permit correction rod 38 to slide freely, that inner diameter is still small enough to provide a bearing-like fit and surface for correction rod 38 within rod housing 37. That is, the inner diameter of blocker 36 is small enough to encircle and contact correction rod 38, but it produces insufficient frictional forces to prevent correction rod 38 from sliding. When it is necessary to rigidly secure correction rod 38 to the spine, heat is applied to blocker 36, causing it to return to its original shape, thereby, increasing the frictional forces between blocker 36 and rod 38 sufficiently to clamp correction rod 38 firmly within rod housing 37.

After the correction rod is segmentally fixed to the patient's spine, the surgical operation is complete. Post-operatively, the rod will apply corrective forces to the patient's spine if it is heated above the shape transition temperature and undergoes transformation to the parent phase crystal configuration. The shape-memory effect is a local phenomena. Thus, localized portions of the rod may be heated selectively in order to produce localized correctional forces applied only at selected vertebral levels. Moreover, by controlling the amount of heat transferred to the rod, the corrective forces may be produced gradually in whatever increments the physician deems appropriate This minimizes the stress which must be borne by the fixation points and hence the probability of failure at the bone-metal interface. The incremental application of correctional forces also allows the physician to monitor the patient for any neural dysfunction as the treatment progresses as well as observe the spinal correction actually produced via fluoroscopy.

The preferred method of heating is a radio frequency induction heater. In such a heater, an alternating current is passed through a coil antenna. A time-varying magnetic field is thus produced which induces eddy currents in the metal rod. The eddy currents then produce heat owing to the electrical resistance of the metal. The frequency of the driving current is selected to be low enough to not produce dipole reversals in water molecules and thus avoid any heating of surrounding tissues. This occurs appreciably only when the electromagnetic waves emitted by the antenna are in the microwave region. The preferred frequency, about 450 $KH_z$, is well below that.

Although the invention has been described in conjunction with the foregoing, many alternatives, variation and modifications are apparent to those of ordinary skill in the art. Those alternatives, variations and modifications are intended to fall within the spirit and scope of the appended claims.

We claim:

1. An apparatus for securing a rod adjacent to a bone, comprising:

a rod housing constructed from shape memory material, said rod housing including a pincer for holding the rod within said rod housing wherein said pincer permits slidable motion of the rod within said rod housing; and a hook constructed from shape memory material, said hook formed integrally with said rod housing in an orientation transverse to said pincer to facilitate the mounting of said rod housing adjacent to the bone.

2. The apparatus according to claim 1 wherein said pincer further is capable of rigidly securing the rod within said rod housing.

3. The apparatus according to claim 1 wherein said pincer defines a semi-circular cavity between its opposed claws for receiving a circular rod therein.

4. The apparatus according to claim 3 wherein, when said claws of said pincer are heated, they encircle the circular rod to hold the circular rod within said rod housing.

5. The apparatus according to claim 1 wherein said pincer defines a straight edged cavity between its opposed claws for receiving a non-circular rod therein.

6. The apparatus according to claim 5 wherein, when said claws of said pincer are heated, they encircle the non-circular rod to hold the non-circular rod within said rod housing.

7. The apparatus according to claim 1 wherein said shape memory alloy comprises nitinol.

8. The apparatus according to claim 1 wherein, when said hook is heated, it encircles the bone to hold said rod housing adjacent to the bone.

* * * * *